United States Patent [19]

Pfeifer

[11] 3,937,725
[45] Feb. 10, 1976

[54] SULPHONIC ACID SALTS WITH ANTISTATIC ACTIVITY

[75] Inventor: Josef Pfeifer, Domat-Ems, GR, Switzerland

[73] Assignee: Inventa AG fur Forschung und Patenverwertung, Zurich, Switzerland

[22] Filed: Aug. 21, 1972

[21] Appl. No.: 282,283

[30] Foreign Application Priority Data

Sept. 6, 1971  Switzerland.................. 13013/71

[52] U.S. Cl.... 260/513 R; 260/512 R; 260/DIG. 21; 260/857 PG
[51] Int. Cl.².................................. C07C 143/11
[58] Field of Search......... 260/513 R, 512 R, 512 C

[56] References Cited
UNITED STATES PATENTS 3,529,039  9/1970  Rinkler et al........................ 260/898
3,706,707  12/1972  Trapasso......................... 260/79.3 R

OTHER PUBLICATIONS

Kirk-Othmer, "Encyclopedia of Chem. Tech.," Vol. 2, pp. 651–653 and 657 (1963).

*Primary Examiner*—Bernard Helfin
*Assistant Examiner*—Nicky Chan
*Attorney, Agent, or Firm*—Jordan B. Bierman; Linda G. Bierman; Kenneth J. Stempler

[57] ABSTRACT

Alkali or alkaline earth metal salts of the reaction product of certain polyalkylene glycols of the formula

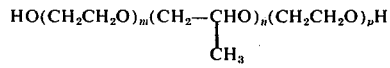

wherein
$n = 0$ to $100$
$(m+p) = 10$ to $500$ $$\frac{n}{m+p} = 0 \text{ to } 3.0$$

with a sultone. These products are superior and long lasting antistatic agents for use in connection with polyamide synthetic fibers.

Polyamides compositions having antistatic properties as well as methods for manufacture of such compositions are also disclosed.

2 Claims, No Drawings

SULPHONIC ACID SALTS WITH ANTISTATIC ACTIVITY

Knitted and woven fabrics of synthetic linear polyamides have excellent properties but suffer from the disadvantage as compared with natural fiber products, of tending to build up an electrostatic charge.

Many attempts have been made to eliminate these undesirable properties by after-treatment or by modification of the polymeric substances concerned (see Swiss Pat. No. 493,684). Thus, for example, a thin film of a hydrophilic or surface-active substance may be applied to the polyamide filaments of knitted or woven fabrics. The antistatic action, however, is of brief duration, and, in particular is not stable to washing (see German Specification 1,056,576). The surface application of polymeric water-insoluble antistatics is also known, but there are substantial technical difficulties to carrying this out. Moreover, the antistatic action is rapidly lost, especially if the material is subject to abrasion (see U.S. Pat. No. 3,473,956).

Another method of solving the problem is by way of the preparation of copolyamide materials; namely, the "polymerising-in" of polyether diamines. However, when such copolymers are produced other properties of the product in question often undergo undesirable changes (see Swiss Pat. No. 438,725).

A process is also known in which the antistatic agent is not polymerised in, but is incorporated in such a way that it is present as a separate phase in the polyamide substance obtained. However, the polyalkylene glycols proposed for this purpose may enter into co-condensation reactions with the polyamide to a certain extent by reason of their terminal functional groups, if they are added during the polycondensation of the polyamide (see U.S. Pat. No. 3,329,557). Such copolycondensation reactions can be avoided by incorporating polyalkylene glycols with terminal ether groups (see Swiss Pat. No. 459,455).

The polyalkylene glycols and their ether derivatives recommended as antistatics have a very low melting viscosity at high temperature, such as for instance the melting points of polyamides. They are difficult to disperse in the polyamide and, on lengthy standing in a melt, have a tendency to separate out. In the working-up of mixtures of polyamides and polyalkylene glycols, such mixtures cause considerable spinning and stretching difficulties. This is especially true if more than 5 percent by weight of polyalkylene glycol has been added.

It has now been found that polyamides with superior and long lasting antistatic properties are obtained if there are added thereto, alkali-metal or alkaline-earth metal salts of reaction products of sultones with polyalkylene glycols of the general formula:

$$HO(CH_2CH_2O)_m(CH_2\underset{\underset{CH_3}{|}}{C}HO)_n(CH_2CH_2O)_pH \qquad I$$

in which n is a whole number from 0 to 100, and (m+p) is a whole number from 10 to 500, and $$\frac{n}{m+p} = 0 \text{ to } 3.0.$$

In particular, the reaction products mentioned have the following general formula:

$$Me-O_3S-R-O(CH_2CH_2O)_m(CH_2\underset{\underset{CH_3}{|}}{C}HO)_n(CH_2CH_2O)_p-R-SO_3-Me \qquad II$$

in which Me is one equivalent of an alkali metal or alkaline-earth metal and preferably lithium, sodium, potassium or calcium; R is an alkylene or an aralkylene group, preferably an alkylene radical with 3 to 4 carbon atoms or the o-benzylene radical; n is a whole number from 0 to 100, (m+p) is a whole number from 10 to 500 and preferably from 20 to 500, and $$\frac{n}{(m+p)} = 0 \text{ to } 3.0$$

and preferably from 0.15 to 1.0. According to the invention, because of the hydrophobic properties of the polypropylene oxide portion of the polyethylene glycol, this portion is to be kept within certain limits by the limitations set forth herein.

Any sultone may be used; for example, gamma butane-sultone, delta butanesultone, tolylsultone, alpha naphthylsultone, alpha naphthylmethanesultone and, preferably, gamma propanesultone.

Suitable as polyethylene glycols are homopolymers of ethylene oxide. Particularly suitable are block copolymers of propylene oxide and ethylene oxide. Such block copolymers, which consist of a central block of polypropylene oxide and two flanking blocks of polyethylene oxide, are available on the market. Polyethyleneglycols of higher molecular weight than those given above are not readily available on the open market.

The preparation of the new polyalkylene glycol dialkylsulphonates is effected by reacting the polyalkylene glycols and the sultones under heat, for example at 150°C; the sulphonic acid formed by alcoholysis being thereafter neutralized, as with alkali hydroxide. More complete reaction is achieved if the sulphonic acid is removed continuously from the reaction mixtrue. This can be achieved by heating the alcoholic constituent and the sultone anhydrous alkali carbonate in an inert solvent such as xylene or dichlorobenzene. It is also advisable to have anhydrous alkali carbonate present.

A preferred procedure is the conversion of the alcoholic constituent into the alkali-metal salt or alkaline-earth metal salt in the presence of an inert solvent and subsequent reaction with the sultone. In this way, the reaction takes place rapidly and quantitatively.

The polyalkylene glycol dialkylsulphonates are substances or pastes which are wax-like at room temperature and which, depending on molecular weight and content of polypropylene oxide units, melt or soften between 20° and 70°C. Compared with the corresponding polyalkylene glycols, the molten mass shows a markedly increased viscosity and remains very viscous and thick liquid at the melting points of the polyamides being treated.

The polyalkyleneglycol dialkylsulphonate can be mixed and dispersed very easily with the polyamide to be treated (polyether disulphonates with a molecular weight of less than 1,000, such as polyethylene glycol 600-0,0'-dipropylsulphonate sodium, begin to be soluble or are already slightly soluble in the polyamide) and, in contrast to the polyalkylene glycols do not show any tendency on standing in a melt to separate out therefrom. They constitute 1 to 15 percent by weight of the mixture of polyamide and disulphonates and preferably 2 – 10 percent by weight, in the treated polyamide. With higher additions, the quality of the product obtained suffers without any material improvement in its antistatic properties.

The disulphonates can be added to the polyamide (preferably a filament-forming or film-forming polyamide such as Polyamide 6, Polyamide 6,6 and Polyamide 12) shortly before the spinning operation. For example, the disulphonate in powder form can be applied to the polyamide chips. Alternatively, the disulphonate can be worked into the finished polyamide, or it can be added to the corresponding melt. As the compounds of the present invention have a very good thermal stability and do not possess any reactive groups, they can also be added directly to the corresponding monomers before the polycondensation, without concern that undesirable side-reactions such as copolymerisation will take place during the polymerisation.

Surprisingly, it has been established that disulphonates (especially those with 20 – 50 percent by weight of polypropylene oxide units per molecule) incorporated in this way are washed out only slightly in the usual extraction of the low molecular weight constituents in the polyamide, so that its antistatic properties are fully preserved.

Other conventional additives may, of course, also be incorporated for stabilization purposes. The usual light stabilizers, heat stabilizers and antioxidants such as manganese salts, triphenyl phosphate and di-t-butyl-p-cresol may be added.

In contrast to the spinning of mixtures of polyamides and polyalkylene glycols, the spinning and stretching of the mixtures produced in accordance with the present invention do not cause difficulties of any kind and do not require any special handling or treatment.

The following Examples are to illustrate the invention and are not intended to be limitative.

| Examples 1–3: | The preparation of antistatics according to the invention |
| Examples 4–5: | The incorporation of these antistatics in the polyamides |
| Example 6: | The spinning properties of polyamides treated according to the invention, and |
| Example 7: | The antistatic properties of polyamides treated in accordance with the invention. |

EXAMPLE 1

750 g. of polyethylene glycol with 30 percent by weight of polypropylene oxide and a molecular weight of 7500 ("Pluronic F 87" of Wyandotte Chem. Corp., U.S.A.), 4.85 g. of sodium metal in 100 ml. of methanol and 1.5 liters of xylene were heated to boiling until all the methanol had been distilled off. 27 g. of propane sultone were then added slowly at the same temperature. An exothermic reaction took place with formation of the disulphonate. After the solvent had been distilled off, 790 g. of the sodium salt of the dipropyldisulphonate compound were left as a white wax-like mass.

| | |
|---|---|
| Molecular weight: | 7800 |
| Softening point: | 30 – 40°C |
| Melting viscosity: | 35 poises |
| | (at 160°C and 1 load) |
| OH number: | < 0.01% |
| | (no OH number measurable) |
| S contant: | 0.85% by weight |
| Solubility in polycaprolactam | < 2% by weight |

The melting viscosity at 160°C, compared with that of "Pluronic F 87", has been increased about 50 times.

EXAMPLE 2

600 g. of polyethylene glycol in accordance with formula I (wherein n=0 and m+p =13), and having a molecular weight of 600 as well as a melting viscosity of 0.017 poise (measured in a rotary viscosimeter at 160°C); 46 g. of sodium metal in 600 ml. of methanol; and 1.2 liters of toluene were reacted in accordance with Example 1 with 244 g. of propane sultone. The reaction product is a wax-like white mass. Compared with the starting polyethylene glycol, the viscosity of the polyethylene glycol-0,0'-dipropylsulphonate sodium obtained has increased by a factor of about 600 to 10.50 poises (rotary viscosimeter, 160°C).

| | |
|---|---|
| Molecular weight: | 890 |
| Solubility in polycaprolactam: | about 6% by weight |
| Softening point: | 25 – 30°C |

EXAMPLE 3

Polyethylene glycol-0,0'-dipropylsulphonate sodium (n = 0) was prepared in accordance with Example 1. The reaction product was a wax-like soft mass.

| | |
|---|---|
| Molecular weight: | 15,000 |
| OH number: | 0.06 % by weight |
| Melting viscosity: | 140 poises |
| | (at 160°C and 1 kp load) |
| Solubility in polycaprolactam: | < 2% by weight |
| Softening point: | 40 – 45°C |

EXAMPLE 4 a. 5 kg. of caprolactam, 500 ml. of water, 500 g. of the antistatic of Example 1 and 2.5 g. of di-t-butyl-p-cresol were mixed in an autoclave with stirring. After careful flushing with nitrogen, the autoclave was closed and heated to 270°C over a period of 2 hours. In the process, an internal pressure of 18 atmospheres gauge was built up. After one hour the pressure was released and further condensation was carried out under atmospheric pressure for another 4 hours at 270°C. The melt was extruded and granulated. The granules were pure white and opaque. The chips obtained were extracted for 24 hours at 80°C with water and then dried for 24 hours at 90°C.

b. 3 kg. of Polyamide 6 granules were mixed with 300 g. of the antistatic of Example 1 and regranulated in an extruder. The granules were thereafter dried for 24 hours at 90°C.

c. 3 kg. of Polyamide 6 granules were regranulated as above with 300 g. of the antistatic of Example 2 and dried.

d. 7 percent by weight of the antistatic of Example 3 was applied as powder to polycaprolactam and the mixture was directly spun. The material was satisfactorily spinnable.

EXAMPLE 5

For comparison purposes, a. 5 kg. of caprolactam were polymerized and made ready for spinning as described in Example 4a, but without the addition of disulphonate.

b. In accordance with Example 4b, 3 kg. of Polyamide 6 granules were regranulated with 300 g. of polyethylene glycol with 30 percent by weight of the polypropylene oxide units used in Example 1 as starting product, and dried.

c. In accordance with Example 4b, 3 kg. of Polyamide 6 granules were regranulated with 300 g. of polyethylene glycol 4000 (molecular weight 4000), and dried.

EXAMPLE 6

The polyamides obtained in accordance with Examples 4 and 5 were spun in known manner from the melt and then stretched to about 3 times their length.

| Polyamide according to | Spinning | Stretching | |
|---|---|---|---|
| | | Fibril fractures per 100 km | Filament fractures per 100 kg |
| Example 4a | normal | 5 | 0 |
| Example 4b | normal | 3 | 2 |
| Example 4c | normal | 3 | 0 |
| Example 4d | normal | 7 | 0 |
| Example 5a (untreated) | normal | 3 | 0 |
| Example 5b (comparison test) | no pressure build-up in the extruder | 80 | 80 |
| Example 5c (comparison test) | no pressure build-up in the extruder | 175 | 125 |

EXAMPLE 7

The antistatic properties of the polyamides obtained according to Examples 4 and 5 were investigated.

| Polyamide according to | Electrostatic charging voltage (V) | Carding test (V) | Ash test |
|---|---|---|---|
| Example 4a | −4 | −20 | does not attract ash |
| Example 4b | −4 | −30 | " |
| Example 4c | −2 | −10 | " |
| Example 4d | | | " |
| Example 5a (untreated) | −262 | +4000 | attracts ash from a distance of 10–15 cm |
| Example 5c (comparison test) | +6 | −750 | does not attract ash |

The electrostatic charging voltage was measured with a Rothschild static voltmeter with a Faraday cup at 20°C and a relative air humidity of 65 percent. The ash test was carried out by rubbing a test strip of the knitted polyamide fabric with wool and then holding it over a fresh finely divided cigarette ash. By means of the carding test, the electrostatic charging voltage in the carding of staple fibers was measured at a distance of 3 cm. Prior to the carding, the staple fibers were freed from the coating of preparation (spinning oil).

Although only a limited number of specific embodiments have been set forth, the invention is to be broadly construed and not to be limited except by the character of the claims appended hereto.

What we claim is:

1. A block copolymeric sulphonic acid salt of the general formula

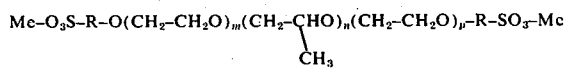

in which Me is one equivalent of an alkali metal or alkaline-earth metal,

R is an alkylene group of 3–4 carbon atoms, n is a whole number from 3–100

(m+p) is a whole number from 20–500

$$\frac{n}{(m+p)} = 0.15 \text{ to } 3.$$

2. Salts according to claim 1 wherein Me is lithium, sodium, potassium or calcium.

* * * * *